(12) United States Patent  
Cunningham (10) Patent No.: US 8,384,892 B2  
(45) Date of Patent: Feb. 26, 2013

(54) SURFACE ENHANCED RAMAN SPECTROSCOPY ON OPTICAL RESONATOR (E.G., PHOTONIC CRYSTAL) SURFACES

(75) Inventor: Brian T. Cunningham, Champaign, IL (US)

(73) Assignee: Board of Trustees of the University of Illinois, Urbana, IL (US)

( * ) Notice: Subject to any disclaimer, the term of this patent is extended or adjusted under 35 U.S.C. 154(b) by 640 days.

(21) Appl. No.: 12/586,516

(22) Filed: Sep. 22, 2009

(65) Prior Publication Data

US 2010/0085566 A1    Apr. 8, 2010

Related U.S. Application Data

(60) Provisional application No. 61/195,133, filed on Oct. 3, 2008.

(51) Int. Cl.
  *G01J 3/44*    (2006.01)
(52) U.S. Cl. ....................................... 356/301
(58) Field of Classification Search .................. 356/244, 356/301, 250, 422, 436, 246; 977/954, 881, 977/762; 724/74, 75, 2.11
See application file for complete search history.

(56) References Cited

U.S. PATENT DOCUMENTS

| | | | |
|---|---|---|---|
| 5,527,712 A * | 6/1996 | Sheehy | 436/525 |
| 6,990,259 B2 | 1/2006 | Cunningham | 385/12 |
| 7,094,595 B2 | 8/2006 | Cunningham et al. | 435/287.2 |
| 7,118,710 B2 | 10/2006 | Cunningham | 422/82.9 |
| 2002/0127565 A1 | 9/2002 | Cunningham et al. | 435/6 |
| 2002/0182716 A1* | 12/2002 | Weisbuch et al. | 435/287.2 |
| 2003/0027327 A1 | 2/2003 | Cunningham et al. | 435/287.2 |
| 2003/0059855 A1 | 3/2003 | Cunningham et al. | 435/7.9 |
| 2006/0034729 A1* | 2/2006 | Poponin | 422/82.05 |
| 2006/0257968 A1 | 11/2006 | Van Duyne et al. | 435/34 |
| 2007/0009380 A1 | 1/2007 | Cunningham | 422/58 |
| 2007/0009968 A1* | 1/2007 | Cunningham et al. | 435/7.9 |
| 2008/0094621 A1* | 4/2008 | Li et al. | 356/301 |
| 2009/0118605 A1 | 5/2009 | Van Duyne et al. | 600/365 |
| 2012/0113419 A1* | 5/2012 | Wang et al. | 356/301 |

OTHER PUBLICATIONS

C. Mathias et al., *Combined enhanced fluorescence and label-free biomolecular detection with a photonic crystal surface*, Applied Optics, vol. 46, pp. 2351-2360 (2007).
N. Ganesh et al., *Enhanced fluorescence emission from quantum dots on a photonic crystal surface*, Nature Nanotechnology, vol. 2, pp. 515-520 (2007).
N. Ganesh et al. *Photonic-crystal near-ultraviolet reflectance filters fabricated by nanoreplica molding*, Applied Physics Letters, vol. 88 (2006).

(Continued)

*Primary Examiner* — Gregory J Toatley
*Assistant Examiner* — Dominic J Bologna
(74) *Attorney, Agent, or Firm* — McDonnell Boehnen Hulbert & Berghoff LLP (57) ABSTRACT

Highly sensitive Surface Enhanced Raman Spectroscopy (SERS) sensors are described in the form of a optical resonator and a metal nanostructure deposited on surface of the optical resonator. In one embodiment the optical resonator is in the form of a photonic crystal, but other optical resonators are contemplated. Examples are described in which the resonant near-fields of a large-area replica molded photonic crystal efficiently couples light from a laser to dielectric-metal "post-cap" nanostructures deposited on the photonic crystal surface by a glancing angle evaporation technique, achieving a high SERS enhancement factor. Other constructions are also contemplated a metal nanostructure formed on a dielectric support deposited on the photonic crystal, including a metallic film deposited over close-packed surface of nanospheres, arrays of metallic nanotriangles, metallic nanorods, metallic nanohelices, arrays of metallic nanospheres, and roughened metal surfaces.

8 Claims, 4 Drawing Sheets

OTHER PUBLICATIONS

C. J. Choi et al., *Single-step fabrication and characterization of photonic crystal biosensors with polymer microfluidic channels*, Royal Society of Chemistry, Lab on a Chip, vol. 6, pp. 1373-1380 (2006).

B. T. Cunningham et al., *Label-free assays on the BIND system*, Journal of Biomolecular Screening, vol. 9, pp. 481-490 (20041.

S. S. Wang et al., *Guided-Mode Resonances in Planar Dielectric-Layer Diffraction Gratings*, Journal of the Optical Society of America a-Optics Image Science and Vision, vol. 7, No. 8, pp. 1470-1474, (1990).

R. Magnusson et al. *New Principle for Optical Filters*, Applied Physics Letters, vol. 61, No. 9, pp. 1022-1024 (1992).

S. S. Wang et al., *Theory and Applications of Guided-Mode Resonance Filters*, Applied Optics, vol. 32, No. 14, pp. 2606-2613 (1993).

C. Y. Wei et al., *Electric field enhancement in guided-mode resonance filters*, Optics Letters, vol. 31, pp. 1223-1225 (2006).

Cunningham et al., *Colorimetric Resonant Reflection as a Direct Biochemical Assay Technique*, Sensor and Actuators B, 81, pp. 316-328 (2002).

Cunningham et al. *A Plastic Calorimetric Resonant Optical Biosensor for Multiparallel Detection of Label Free Biochemical Interactions*, Sensors and Actuators B, 2002, v. 85, pp. 219-226.

Haynes et al., *Surface-enhanced Raman Sensors: early history and the development of sensors for quantitative biowarfare agent and glucose detection*, Journal of Raman Spectroscopy, vol. 36 pp. 471-484 (2005).

J. G. W. v. d. Waterbeemd et al., *Effect of the Mobility of Metal Atoms on the Structure of Thin Films Deposited at Oblique Incidence*, Philips Res. Rep., vol. 22, pp. 375-387 (1967).

K. Robbie et al. *Fabrication of Thin-Films with Highly Porous. Microstructures*, Journal of Vacuum Science &.Technology A, vol. 13, No. 3, pp. 1032-1035 (1995).

L. Abelmann et al., *Oblique evaporation and surface diffusion*, Thin Solid Films, vol. 305, pp. 1-21 (1997).

U.S. Appl. No. 13/438,950, Cunningham et al., filed Apr. 4, 2012.

U.S. Appl. No. 13/438,969, Cunningham et al., filed Apr. 4, 2012.

\* cited by examiner

SURFACE ENHANCED RAMAN SPECTROSCOPY ON OPTICAL RESONATOR (E.G., PHOTONIC CRYSTAL) SURFACES

PRIORITY

This application claims priority benefits under 35 U.S.C. §119(e) to U.S. Provisional application Ser. No. 61/195,133 filed Oct. 3, 2008, the content of which is incorporated by reference herein.

STATEMENT REGARDING FEDERALLY SPONSORED RESEARCH OR DEVELOPMENT

Not applicable.

BACKGROUND

Raman spectroscopy is a general-purpose detection technique in which electrons within a molecule are oscillated by an externally applied electric field from a laser, and though collisions between oscillating electrons and atomic nuclei of the molecule, the molecule begins to vibrate. Molecules in vibration are in a slightly elevated energy state compared to their ground state. The difference in energy between vibrational energy states and the ground state can be measured by determining the difference in energy between incident photons and scattered photons, a quantity known as the "Raman Shift." Because molecules, especially complex ones, can vibrate along many different directions (called "vibrational modes"), there is not a single excited vibrational state, but rather a multitude of them, with each vibrational mode represented by a different Raman shift. Therefore, every molecule has a unique "Raman Spectrum" that may serve as a fingerprint to identify the molecule through its vibrational energy spectrum. Because the incidence of electron/nucleus collisions that result in transfer of momentum to the molecule is extremely rare, Raman scattered photons intensity is typically extremely low, and high energy lasers are required to obtain measurable Raman spectra.

Surface Enhanced Raman Spectroscopy (SERS) utilizes a metal surface to increase the interaction between the incident laser electric field and measured molecules by several orders of magnitude, thus resulting in Raman spectra that are more easily observable. Most commonly, SERS is performed on roughened metal surfaces or on the surface of metal nanoparticles, because these surfaces are capable of generating Surface Plasmon Resonance (SPR). The mechanism for SERS is not completely understood, but a common hypothesis is that electrons in the metal are excited to oscillate by the applied laser electric field (thus generating SPR), and that the metal SPR electrons can more effectively transfer their momentum to molecules that are adsorbed to the metal surface. Another hypothesis is that the surface plasmons generate locally high electric fields on the metal surface (higher than the incident laser electric field) that in turn provide greater electron oscillation within adsorbed molecules for SERS measurement.

Photonic crystals, also commonly referred to as photonic bandgap structures, are another class of sensor devices based on periodic dielectric structures exhibiting a spatially periodic variation in refractive index that forbids propagation of certain frequencies of incident electromagnetic radiation. The photonic band gap of a photonic crystal refers to the range of frequencies of electromagnetic radiation for which propagation through the structure is prevented. The photonic band gap phenomenon may be conceptualized as complete or partial reflection of incident electromagnetic radiation having selected frequencies due to interaction with the periodic structural domains of a photonic crystal. The spatial arrangement and refractive indices of these structural domains generate photonic bands gaps that inhibit propagation of electromagnetic radiation centered about a particular frequency.

Photonic crystals provide an electromagnetic analog to electron-wave behavior observed in crystals wherein electron-wave concepts, such as dispersion relations, Bloch wave functions, van Hove singularities and tunneling, having electromagnetic counterparts in photonic crystals. In semiconductor crystals, for example, an electronic band gap of energy states for which electrons are forbidden results from a periodic atomic crystalline structure. By analogy, in a photonic crystal, a photonic band gap of forbidden energies (or wavelengths/frequencies) of electromagnetic radiation results from a periodic structure of a dielectric material, where the periodicity is of a distance suitable to interact with incident electromagnetic radiation.

Selection of the physical dimensions, refractive indices and spatial distribution of structural domains of a photonic crystal provides an effective means of designing a photonic crystal a photonic band gap with a selected frequency distribution. One-dimensional, two-dimensional and three-dimensional photonic crystals have been fabricated providing complete or at least partial photonic band having selected frequency distributions gaps in one or more directions. Photonic crystals have also been fabricated having selected local disruptions (e.g., missing or differently-shaped portions of the structural domains of periodic array) in their periodic structure, thereby generating defect or cavity modes with frequencies within a forbidden bandgap of the crystal. Photonic crystals having specific defects are of particular interest because they provide optical properties useful for controlling and manipulating electromagnetic radiation, such as the ability to provide optical confinement and/or wave guiding with very little, or substantially no, radiative losses.

As diffraction and optical interference processes give rise to the photonic band gap phenomenon, the periodicity of photonic crystal structures is typically on the order of the wavelength of incident electromagnetic radiation. Accordingly, photonic crystals for controlling and manipulating visible and ultraviolet electromagnetic radiation typically comprise dielectric structures with periodic structural domains having submicron physical dimensions on the order of 100s of nanometers. A number of fabrication pathways for making periodic structures having these physical dimensions have been developed over the last decade, including micromachining and nanomachining techniques (e.g., lithographic patterning and dry/wet etching, electrochemical processing etc.), colloidal self assembly, replica molding, layer-by-layer assembly and interference lithography. Advances in these fabrication techniques have enabled fabrication of one-dimensional, two-dimensional and three-dimensional photonic crystals from a range of materials including dielectrics, metal oxides, polymers and colloidal materials.

Because PC sensors are comprised of dielectric materials, they will not quench fluorophores within <30 nm of their surface by resonant energy transfer, and they can exhibit high Q-factors due to their low absorption loss. One embodiment is comprised of a one-dimensional (1D) or two-dimensional (2D) periodic surface structure formed from a low refractive index (RI) dielectric material that is overcoated with a high RI thin film, these devices can be fabricated upon plastic substrates inexpensively over large areas by a nanoreplica molding process and incorporated into the surface of glass slides, microfluidic channels, and microtiter plates. The device period, grating depth, film thicknesses, and RIs of the materials are chosen in such a way that the PCs can support guided-mode resonances at designated wavelengths, where the device reflects ~100% of incident light at the resonant wavelengths with all other wavelengths being transmitted. Under resonant conditions, excited leaky modes are localized in space during their finite lifetimes, which enhances the near electric-field intensity of the PC structure and thus enhances the excitation of fluorophores near the PC surface.

Further background information relating to photonic crystals sensors and their properties and methods of manufacture are disclosed in the following references, which are incorporated by reference herein: P. C. Mathias, N. Ganesh, L. L. Chan, and B. T. Cunningham, "Combined enhanced fluorescence and label-free biomolecular detection with a photonic crystal surface," *Applied Optics*, vol. 46, pp. 2351-2360, 2007; N. Ganesh, W. Zhang, P. C. Mathias, E. Chow, J. A. N. T. Soares, V. Malyarchuk, A. D. Smith, and B. T. Cunningham, "Enhanced fluorescence emission from quantum dots on a photonic crystal surface," *Nature Nanotechnology*, vol. 2, pp. 515-520, 2007; N. Ganesh and B. T. Cunningham, "Photonic-crystal near-ultraviolet reflectance filters fabricated by nanoreplica molding," *Applied Physics Letters*, vol. 88, 2006; C. J. Choi and B. T. Cunningham, "Single-step fabrication and characterization of photonic crystal biosensors with polymer microfluidic channels," *Lab on a Chip*, vol. 6, pp. 1373-1380, 2006; B. T. Cunningham, P. Li, S. Schulz, B. Lin, C. Baird, J. Gerstenmaier, C. Genick, F. Wang, E. Fine, and L. Laing, "Label-free assays on the BIND system," *Journal of Biomolecular Screening*, vol. 9, pp. 481-490, 2004; S. S. Wang, R. Magnusson, J. S. Bagby, and M. G. Moharam, "Guided-Mode Resonances in Planar Dielectric-Layer Diffraction Gratings," *Journal of the Optical Society of America α-Optics Image Science and Vision*, vol. 7, pp. 1470-1474, 1990; R. Magnusson and S. S. Wang, "New Principle for Optical Filters," *Applied Physics Letters*, vol. 61, pp. 1022-1024, 1992; S. S. Wang and R. Magnusson, "Theory and Applications of Guided-Mode Resonance Filters," *Applied Optics*, vol. 32, pp. 2606-2613, 199; C. Y. Wei, S. J. Liu, D. G. Deng, J., Shen, J. D. Shao, and Z. X. Fan, "Electric field enhancement in guided-mode resonance filters," *Optics Letters*, vol. 31, pp. 1223-1225, 2006.

Biosensors incorporating photonic crystal structures are described in the following references which are hereby incorporated by reference in their entireties: U.S. Pat. Nos. 7,118,710, 7,094,595, and 6,990,259; U.S. Published applications 2007/0009968; 2002/0127565; 2003/0059855; 2007/0009380; 2003/0027327; and Cunningham, B. T., P. Li, B. Lin and J. Pepper, Colorimetric Resonant Reflection as a Direct Biochemical Assay Technique, Sensor and Actuators B, 2002, 81, pgs 316-328; and Cunningham, B. T. J. Qiu, P. Li, J. Pepper and B. Hugh, A Plastic Calorimetric Resonant Optical Biosensor for Multiparallel Detection of Label Free Biochemical Interactions, Sensors and Actuators B, 2002, v. 85, pgs 219-226.

SUMMARY

The invention describes a new way to couple enhanced electric fields to metal nanostructures for SERS. We describe here the first use of a dielectric-based optical resonator (photonic crystal, abbreviated PC herein), to provide an enhanced electric field that in turn can couple to metal nanostructures formed on the PC surface. The PC is designed to have an optical resonance at the same laser wavelength that is used to excite SERS vibrations in detected molecules. The PC is capable of storing energy from the laser within its structure, and confining it within its structure. Through design of the PC structure, part of the confined energy will extend out of the PC surface, and into the surrounding medium, where the extended energy magnitude decays exponentially as one moves away from the PC surface. This region of extended energy is known as the "evanescent field" of the photonic crystal at its resonant wavelength.

We demonstrate in this disclosure that metal nanostructures located within the evanescent field region of the optical resonator (e.g., PC) experience greater excitation than metal nanostructures that are not excited by the PC resonant phenomenon, resulting in additional enhancement of SERS for molecules adsorbed or deposited on the nanostructures. That is, an enhanced resonant electric field produced by the optical resonator in response to in-coupled incident radiation is coupled to the metal nanostructures, thereby increasing the sensitivity of the device to surface enhanced Raman spectroscopy signals of a molecule that is absorbed or deposited on the sensor surface. Thus, these optical resonators, such as photonic crystals, provides a sensor structure and means for further enhancement of SERS—a technique referred to as "PC-SERS." While the effect of enhancing the excitation of SERS using a photonic crystal optical resonator has been demonstrated, in principle, any optical resonator could provide the same effect. Such other optical resonators include whispering gallery mode spheres, microring resonators, photonic crystal fibers, microdisk resonators, and microtoroid resonators. Higher quality factor (Q factor) optical resonators are expected to provide increased benefit for SERS enhancement.

One of the purposes of the sensor devices of this invention is to increase the sensitivity of SERS signals for any type of measured molecule, deposited on the sensor surface. There are a wide variety of existing applications for SERS which will benefit from the increased sensitivity, including detection of molecules in the picomole to femtomole range, detecting trace quantities of explosives, drugs-of-abuse, environmental contaminants, and biological pathogens. The technique is increasingly used for manufacturing quality control (especially for food and pharmaceuticals), life science research (for detecting proteins, DNA, RNA, and the development of Raman "tags" for other biomolecules), and clinical diagnostic tests (through observing Raman spectra of cancer cells, various types of tissue, bacteria, and viruses). Any molecule that is currently detectable by SERS will be detectable with greater sensitivity if performed on a PC-SERS device of this disclosure.

Another aspect of this disclosure is novel methods of sensor fabrication are described, including the incorporation of dielectric-metal "post-cap" nanostructures on an optical resonator sensor. In one embodiment, the optical resonator is a photonic crystal. A photonic crystal SERS sensor device of this disclosure can be fabricated inexpensively over large surface areas using a nanoreplica molding approach. The embodiment of SERS nanostructure comprises of a dielectric post and metal cap is only one possible embodiment of a metallic nanostructure that would provide a greater SERS enhancement effect when applied to a PC surface. Other configurations are possible. For example, metallic films deposited over a close-packed surface of nanospheres (also called "Ag Film Over Nanospheres" or AgFON) as disclosed in Van Duyne et al., U.S. patent application publication 2009/0118605 and U.S. Patent application publication 2006/0257968), arrays of metallic nanotriangles (see Haynes et al., Surface-enhanced Raman Sensors: early history and the development of sensors for quantitative biowarfare agent and glucose detection, J. Raman Spectrosc. 2005 vol. 36 pp. 471-484), metallic nanorods, metallic nanohelices, arrays of metallic nanospheres, roughened metal surfaces, or other SERS-acvtive surface can be applied to a PCT to magnify or enhance the SERS signal.

Additionally, a PC-SERS sensor of this disclosure can be incorporated as a surface of a wide variety of liquid media handling devices, including microscope slides, microfluidic channels, microtiter plates, flasks, product containers, Petri dishes, the internal surface of tubing, and test tubes. For example, the sensor is incorporated into a support structure that provides a base for the Petri dish or the bottom of the wells of a 96 well microtiter plate. The sample to be tested is placed into the dish or well of the plate into contact with the PC-SERS sensor.

In one specific aspect, a method is described for performing surface enhanced Raman spectroscopy (SERS) with enhanced sensitivity, comprising the steps of: providing an optical resonator device having a metal nanostructure formed on the optical resonator device, illuminating the optical resonator device with light to produce an enhanced resonant electric field in the optical resonator device; and coupling the enhanced electric field to the metal nanostructure. In one embodiment, the optical resonator device comprises a photonic crystal. In another embodiment, the metal nanostructure is formed on a dielectric support deposited on the photonic crystal.

In another specific aspect, a method of manufacturing a SERS sensor is disclosed comprising the steps of fabricating an optical resonator (e.g., a photonic crystal having a periodic grating surface), and depositing a metal nanostructure on the surface of the optical resonator. In one specific embodiment, the method further comprises the step of depositing a multitude of dielectric supports onto the surface of the optical resonator, the supports having a peripheral portion, and wherein the depositing step comprises the step of depositing metal nanostructures on the peripheral portions of the dielectric supports.

In yet another aspect, a surface enhanced Raman spectroscopy sensor is disclosed comprising an optical resonator having a metal nanostructure formed on the surface of the optical resonator, wherein an enhanced resonant electric field produced by the optical resonator in response to in-coupled incident radiation is coupled to the metal nanostructure. In preferred embodiments the optical resonator comprises a photonic crystal. A dielectric support is deposited on the surface of the photonic crystal and the metal nanostructure is deposited on the peripheral portion of the dielectric support.

DETAILED DESCRIPTION OF PREFERRED EMBODIMENT

Figure 1A:
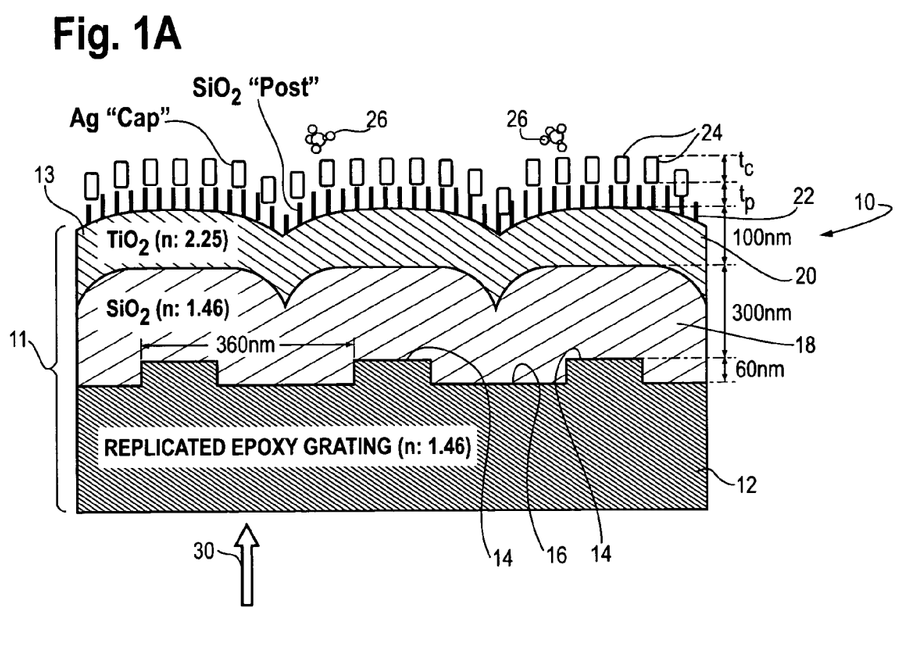
FIG. 1(a) is a schematic, cross-sectional diagram of PC-SERS sensor in accordance with a representative but not limiting example of this invention.

FIG. 1(a) shows a cross sectional schematic of the PC-SERS sensor or substrate 10 in accordance with a representative embodiment. The sensor 10 includes an optical resonator, which in the illustrated embodiment is in the form of a photonic crystal 11 consisting of a periodic surface grating (replicated epoxy grating) 12. The grating 12 is supported from below by a clear plastic support (not shown, e.g., polyethylene terephthalate, or glass). The photonic crystal 11 includes a relatively thick $SiO_2$ layer 18 deposited on the grating 12, and a high index of refraction material layer 20 (e.g., $TiO_2$) deposited on the layer 18. A $SiO_2$ dielectric post layer 22 is deposited on the photonic crystal 11 (i.e., on the upper surface 14 of the layer 20) and a metal nanostructure 24 (Ag "cap") is deposited on the dielectric post layer 22. The thicknesses of the various layers in FIG. 1A are not necessarily to scale. The thickness of $SiO_2$ post layer 22 is 50 nm and that of Ag cap 24 is 30 nm in the illustrated example.

The PC 11 has a 1-dimensional periodic surface grating consisting of alternating high and low regions 14, 16 and extends into the plane of the page. The $SiO_2$ layer 22 and the metal nanostructure layer 24 form a "post-cap" nanostructure coating on the surface 13 of the PC sensor 11, where $t_p$ is the $SiO_2$ post (22) thickness and $t_c$ is the Ag cap (24) thickness.

The present disclosure demonstrates that the resonant near-fields of a large-area replica molded Photonic Crystal (PC) sensor 11 (FIG. 1A) can efficiently couple light 30 from a laser to $SiO_2$—Ag "post-cap" nanostructures (22 and 24, FIG. 1a) deposited on the photonic crystal 11 surface for achieving a high Surface Enhanced Raman Spectroscopy (SERS) enhancement factor (abbreviated "EF" herein). To examine the feasibility of the PC-SERS sensor of FIG. 1A, the Raman spectrum of trans-1,2-bis(4pyridyl)ethane (BPE) was measured and compared with that from an ordinary glass substrate coated with the same $SiO_2$—Ag nanostructures. The results are presented below. An optimization study for the dimensions of the $SiO_2$ posts 22 and Ag caps 24 was conducted and the results are also presented below.

Since the first experimental demonstrations of SERS, it has been shown that many molecules display Raman cross-sections that are several orders of magnitude greater when adsorbed upon roughened conducting surfaces than the corresponding quantity in solution or on an ordinary smooth surface. Due to the surface enhancement, small sample volumes can be detected with concentration resolution in the picomole to femtomole range, making the SERS technique potentially attractive for detecting trace quantities of explosives; drugs-of-abuse, environmental contaminants, and biological pathogens. In FIG. 1A, such molecules to be analyzed are shown at 26. For purposes of confinement of a liquid sample containing the molecules 26, the PC-SERS sensor 10 of FIG. 1 may be incorporated or integrated into a fluid handling vessel such as microscope slide, test tube, petri dish, microtitre plate well, or other testing format.

The SERS substrate surface nanostructure is the key element for obtaining high enhancement factors, and a wide variety of configurations have been used. The mechanisms by which the SERS effect occur are currently a subject of debate, and two main enhancement routes have been proposed—namely the electromagnetic (EM) effect and the chemical enhancement (CE) effect. This work is concerned only with the EM effect, in which the local electromagnetic field at the surface of a metal is significantly changed from that of the incident field, and becomes more pronounced when fine metal particles or rough surfaces generate local surface plasmon resonances. The EM effect results in enhanced excitation of Raman vibrational modes due to highly localized electromagnetic fields that can be substantially higher than the electric field of the incident laser illumination.

An extensive literature exists on the effects of metal surfaces for SERS and fluorescence enhancement, and on the use of a variety of metal surface configurations (planar, corrugated, colloidal) or metallic particle types (spheres, shells, boxes, and triangles to name just a few) that involve plasmonic resonances to enhance EM excitation. However, surface plasmons present an inherent characteristic that is not optimal for SERS. The spectral width of surface plasmon resonances is generally large (~100 nm) due to the lossy nature of metals—essentially implying a resonance with a very low quality factor (Q-factor). As an optical resonator, low Q-factor results in relatively low stored electric field intensity, as energy is quickly dissipated in the metal. Although dielectric-based optical resonators can achieve high Q-factors and high field intensities, they have not been previously exploited for SERS.

Resonances occurring in periodic dielectric nanostructures have recently gained importance for a wide range of sensing, filtering and feedback applications. Among such resonant nanostructures, the guided-mode resonance filter (GMRF) based on one-dimensional and two-dimensional photonic crystal (PC) slabs has been the subject of intense study. Although the far-field manifestation of the resonance as a strong narrow linewidth reflection peak is well studied, few papers report on the near-field characteristics of such devices. We have recently shown that PC resonant near-fields at the absorption wavelength of fluorophore can greatly enhance the detection sensitivity of fluorescent-tagged molecules.

The guided-mode resonance (GMR) effect occurs in PC sensors like those described in this document when evanescent (cut-off) diffracted orders of a periodic sub wavelength surface structure couple to the modes of an effective high index layer (layer 20 in FIG. 1A). The energy is coupled to 'leaky modes' which escape from the structure due to its diffractive nature in both the forward and backward directions and interfere with the directly transmitted and specularly reflected zeroth orders, leading to a strong reflection about a resonant wavelength whose line width and spectral location are set by the physical parameters of the device. Like other optical resonances, the GMR effect leads to storage of energy within the resonator under steady-state conditions, the magnitude of which is directly related to the resonance Q-factor, which can be as high as 2000 for a GMR filter.

In this disclosure, it is demonstrated that the near-fields of a PC slab optical resonator (FIG. 1*a*) can efficiently couple light from a laser to metal nanostructures (24) deposited on the PC surface for enhanced SERS. The Glancing Angle Deposition (GLAD) technique is used in the illustrated embodiment to create a high density coating of electrically isolated Ag nanoparticles 24 that are supported vertically from the PC surface 13 (uppermost surface of the TiO$_2$ layer 20) by means of 0-75 mm-tall SiO$_2$ dielectric posts 22. (The range of 0-75 nm for the thickness or height $t_p$ of the dielectric posts 22 indicates that such posts are optional (0 nm); the upper value of 75 nm is considered a preferred embodiment but the height $t_p$ may in fact be greater than that value in other embodiments). In a preferred embodiment in which the posts 22 are present, GLAD is used to deposit both the posts 22 and the metal nanostructures 24.

GLAD is a physical vapor deposition technique in which the angle between the incoming flux and the surface of the substrate is set to be typically less than 15°. The technique is described in the following references, incorporated by reference herein: J. G. W. v. d. Waterbeemd and G. W. v. Oosterhout, "Effect of the Mobility of Metal Atoms on the Structure of Thin Films Deposited at Oblique Incidence," *Philips Res. Rep.*, vol. 22, pp. 375-387, 1967; K. Robbie, L. J. Friedrich, S. K. Dew, T. Smy, and M. J. Brett, "Fabrication of Thin-Films with Highly Porous Microstructures," *Journal of Vacuum Science & Technology α-Vacuum Surfaces and Films*, vol. 13, pp. 1032-1035, 1995. L. Abelmann and C. Lodder, "Oblique evaporation and surface diffusion," *Thin Solid Films*, vol. 305, pp. 1-21, 1997.

To examine the feasibility of the PC-SERS substrate, a Raman spectrum of trans-1,2-bis(4pyridyl)ethane (BPE) on the PC-SERS sensor 10 of FIG. 1 was measured and compared with that from an ordinary glass substrate coated with the same SiO$_2$—Ag structure, and an optimization study for the dimensions of the SiO$_2$ posts 22 and Ag caps 24 was conducted.

Figure 2A:
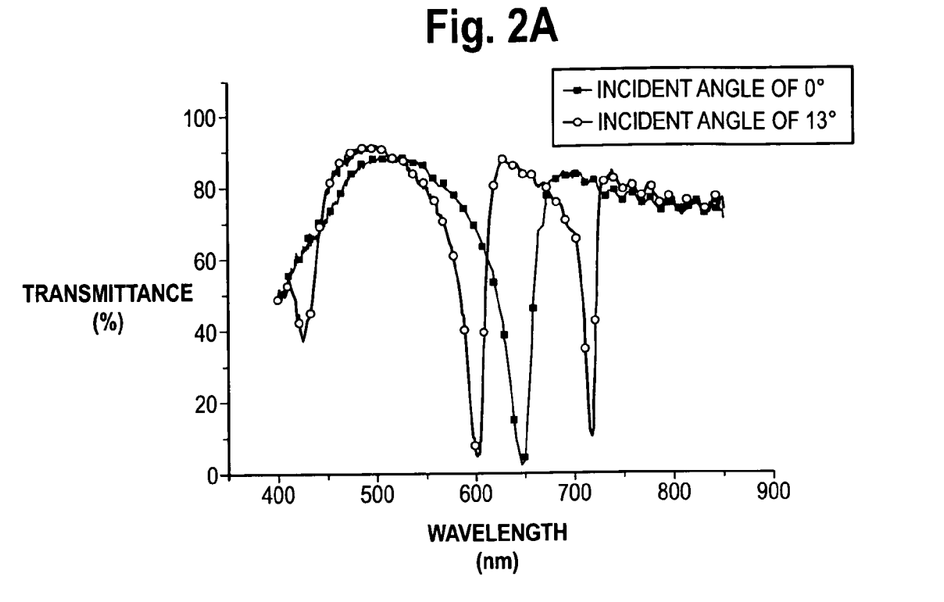
FIGS. 2(a) and 2(b) are a comparison of measured transmission spectra (FIG. 2(a)) from a bare PC (without the post layer 22 and Ag cap 24) at the incident angles of 0° and 13°, and (FIG. 2(b)) from PC-SERS substrate with $SiO_2$—Ag nanostructure ($t_p$=50 nm, $t_c$=40 nm) and with only Ag nanostructure ($t_c$=40 nm) at the incident angle of 13°; the TE polarized broad band light source was used for the measurement.

To fabricate the PC, a polymer grating layer 12 (period=360 nm, depth=60 nm) was fabricated using a nanoreplica molding process as described in previous work from a silicon grating template. Following replication of the grating structure, a SiO$_2$ layer 18 with a thickness of ~300 nm (n=1.46) and a TiO$_2$ layer 20 with a thickness of ~100 nm (n=2.25) were subsequently deposited over the grating surface (regions 14, 16) by sputtering. The purpose of the SiO$_2$ layer 18 is to physically separate the resonant near fields from the polymer material forming the grating layer 12 to reduce the intensity of undesired background fluorescence from the polymer. The resulting PC slabs 11 have a resonant reflection for the laser used to excite SERS (λ=600 nm, TE polarized (electric field vector parallel to the grating lines)) at an incident angle of ~13°, as shown in FIG. 2(*a*). Following PC fabrication, GLAD coatings of SiO$_2$ (20) and Ag (24) were applied using an electron-beam deposition system (Temescal) at a deposition rate of 5 Å/s for both materials. The angle between the incoming flux of evaporated material and the device surface 13 was 5.0°. To minimize the shadowing effect of grating lines, the incoming flux was parallel to the grating sidewalls (vertical walls forming the raised portions 14).

Figure 1B:
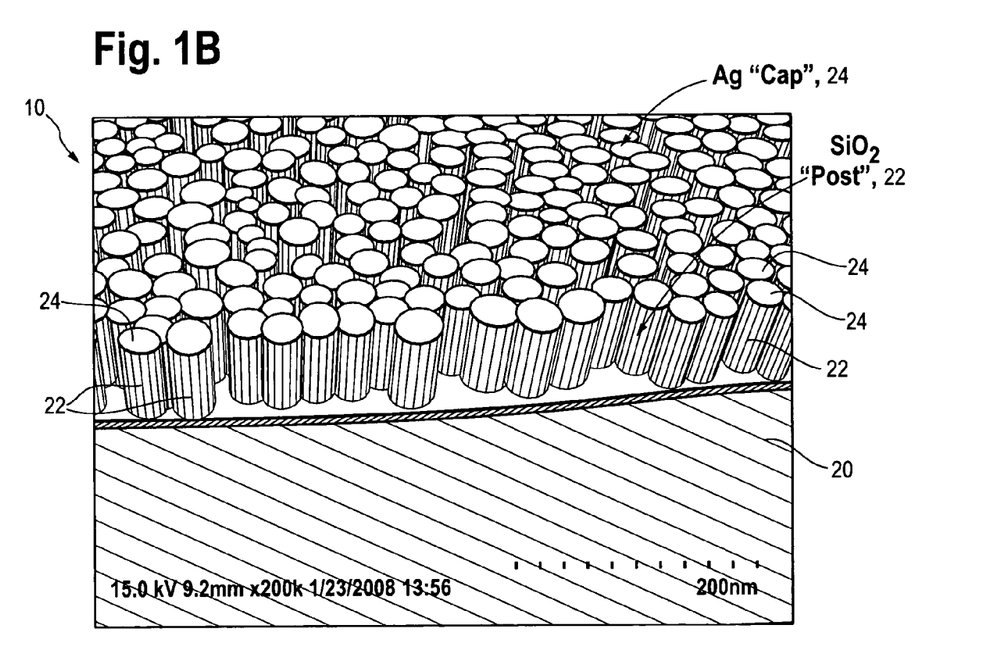
FIG. 1(b) is a SEM image of the PC-SERS sensor 10 of FIG. 1(a), showing the $SiO_2$ posts 22 extending away from the surface of the photonic crystal sensor and the Ag "cap" metal nanostructures 24 deposited on the peripheral portions of the posts 22.

FIG. 1(*b*) shows the cross sectional scanning electron microscope (SEM) image of a typical SiO$_2$—Ag "post-cap" nanostructure (22, 24) ($t_p$=50 nm, $t_c$=30 nm), fabricated on a silicon substrate. Since the diameter and density of the GLAD nanostructures are determined by both the deposition angle, and the atomic mobility, we obtain SiO$_2$—Ag "post-cap" structures in which the diameter of Ag regions 24 is greater than the SiO$_2$ support post 22.

Figure 2B:
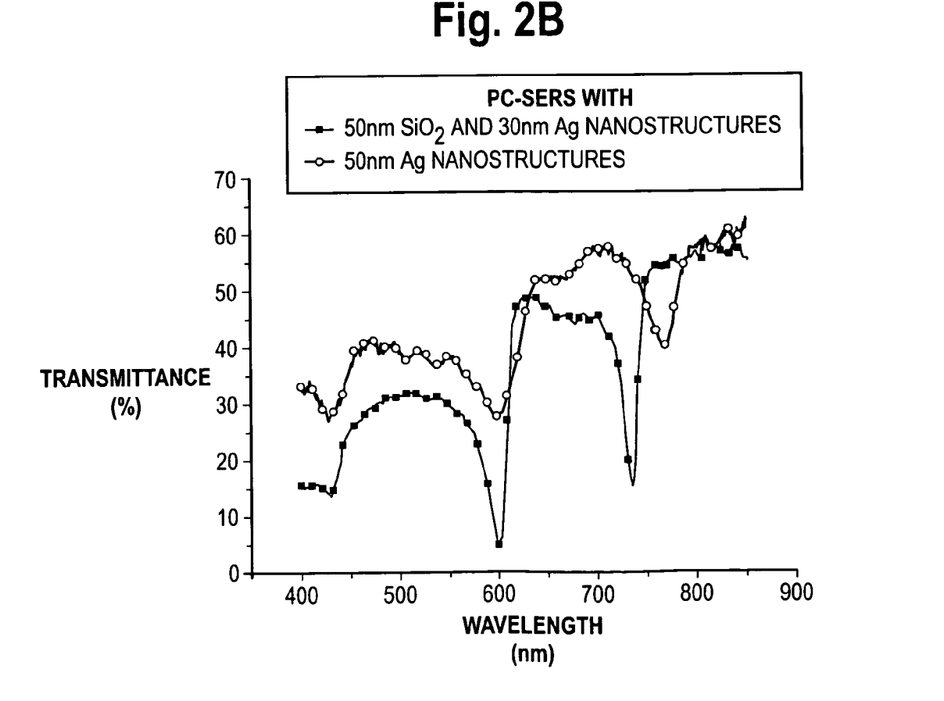

The function of the SiO$_2$ post 22 is to prevent quenching of resonant near-fields of the PC due to the high-loss metal nanostructures 24. To examine the effects of the SiO$_2$ post 22 height $t_p$ on the PC resonance characteristics, the transmission spectra of the PC-SERS substrate with Ag nanostructures without SiO$_2$ posts ($t_p$=0 nm, $t_c$=30 nm), and with 50 nm SiO$_2$ posts ($t_p$=50 nm, $t_c$=30 nm) were measured and compared as depicted in FIG. 2(b). FIG. 2(b) shows that the full width at half-maximum (FWHM) of the PC resonance increases from $\Delta\lambda$=32 nm to $\Delta\lambda$=60 nm as the SiO$_2$ post height decreases from $t_p$=30 to $t_p$=0 nm, resulting in reducing Q-factor from Q=18.75 to Q=10. Therefore, a balance must be achieved between locating the Ag nanostructures too close to the PC surface (to maintain resonant near field coupling of the Raman laser to the PC) while still positioning them within the PC evanescent field.

The Raman detection instrument was comprised of a TE polarized Argon-dye laser excitation source (Coherent, INNOVA-90 and CR-500, $\lambda$=600 nm, Output power=82 mW), a sample holder with a rotational stage, a power meter to measure laser transmittance through the sample, imaging optics, a spectrometer (SPEX-Triplemate), and a cooled CCD (Princeton Instruments). The instrumentation is shown in the Appendix to this document Raman scattered light was collected from a 235.4×51.8 $\mu$m$^2$ area, and the diameter of the laser beam spot was ~470 $\mu$m. A 5 $\mu$L droplet of BPE dissolved in methanol (0.00636 M) was applied to each substrate by pipette. The BPE/methanol droplet spread out to form a circular region with a diameter of ~1.6 cm on the substrate, resulting in a density of ~9.5 10$^{15}$ molecules/cm$^2$. For a laser wavelength of $\lambda$=600 nm, the PC resonance could be excited by illuminating at an angle of ~±13°, and precise tuning to the "On-Resonance" condition for any substrate could be achieved by adjustment of the rotation stage to obtain a minima in laser transmitted intensity through the PC. "Off-Resonance" conditions were obtained by detuning the incident angle from the transmission minima by ~±13°.

Figure 3A:
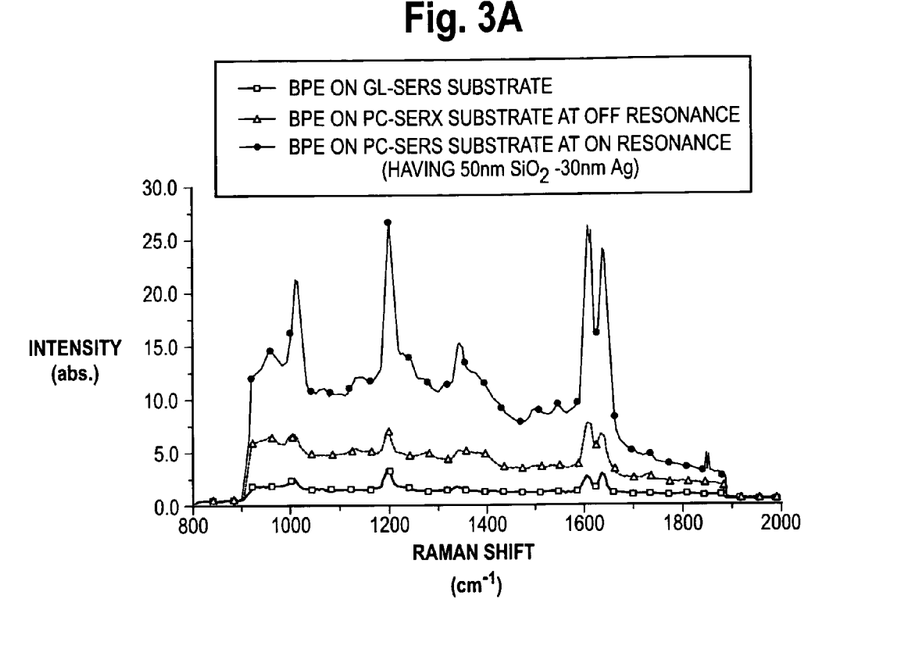
FIG. 3(a) is graph of the Raman spectra of trans-1,2-bis (4pyridyl)ethane (BPE) on a GL-SERS substrate and a PC-SERS substrate at On and Off resonance condition.

To determine the additional SERS enhancement effects due to the PC, the Raman spectrum of BPE on a PC-SERS substrate was compared with that from an ordinary glass slide prepared with the SiO$_2$—Ag nanostructure (GL-SERS) substrate. FIG. 3(a) shows the Raman spectra obtained from BPE using both GL-SERS and PC-SERS substrates at On- and Off-resonance conditions. The thickness of the SiO$_2$ post layer was 50 nm and that of the Ag cap layer was 30 nm for both substrates. The Raman peaks at 1000, 1200, 1610 and 1639 cm$^{-1}$ can be found in all spectra in FIG. 3(a) and these peaks correspond to the ring-breathing mode of pyridine, the C=C stretching mode, the aromatic ring stretching mode, and the in-plane ring mode, respectively. The Raman signal was defined as the integrated intensity of the 1200 cm$^{-1}$ peak after subtraction of the background noise.

In FIG. 3(a), the Raman signal obtained from the PC-SERS substrate at the Off-resonance condition is nearly the same as the signal from the GL-SERS substrate, thus there is no enhanced EM near-field due to the PC, as expected. However, at the On-resonance condition of PC-SERS substrate, the Raman signal increased significantly.

Figure 3B:
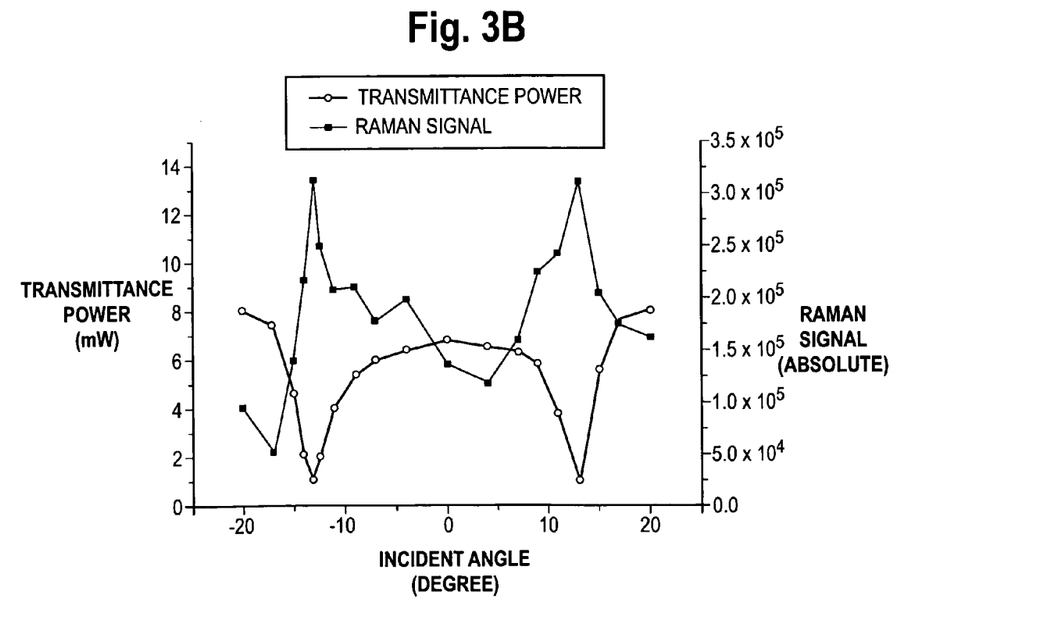
FIG. 3(b) is a graph providing a comparison of Raman signal and transmission power obtained from PC-SERS substrate for varying incident angle; GL-SERS and PC-SERS substrates have same $SiO_2$—Ag nanostructure ($t_p$=50 nm, $t_c$=30 nm).

FIG. 3(b) compares the Raman signal and transmitted power through the PC-SERS substrate with SiO$_2$—Ag nanostructures ($t_p$=50 nm, $t_c$=30 nm) for varying incident angles, showing the relationship between the Raman signal and enhanced EM near-fields from the PC. The transmitted power of the laser is minimized at the resonance angle, ±13° and at those incident angles, the Raman signal is maximized. These results demonstrate that a PC-SERS substrate can substantially enhance SERS sensitivity.

An optimization study for the dimensions of the SiO$_2$—Ag nanostructure (post 22 and caps 24) was conducted to maximize the SERS Enhancement Factor (EF). The SERS EF can be defined as EF=$I_{SERS}/t_{SERS}N_{SERS})(I_{Ref}/t_{Ref}N_{Ref})^{-1}$, where, $I_{SERS}$ is the Raman signal from the SERS substrate, $I_{Ref}$ is the Raman signal from a reference substrate, t is the detection integration time for each measurement, and the N is the number of excited molecules. To establish a baseline from which EF attributable to either the PC or the SiO$_2$—Ag nanostructure could be calculated, two references were required. For a baseline reference, the Raman signal from a droplet of BPE in methanol, at a high concentration (0.636 M), on a plain glass surface was used, denoted by $I_0$. A second reference, denoted by $I_{Nano}$, was obtained by measuring the SERS signal on a GL-SERS substrate with a 100× lower BPE concentration (0.00636 M). The enhancement factor attributed only to the post-cap nanostructure coating is therefore $EF_{Nano}$=100 $(I_{Nano}t_0)/(I_0 t_{Nano})$. The Raman signal of the PC-SERS substrate, obtained from the Raman spectrum at the On-resonance condition using 0.00636 M BPE is denoted by $I_{PC-SERS}$. The EF due to the effects of the PC is given by $EF_{PC-SERS}$= $(I_{PC-SERS}t_{Nano})/(I_{Nano}t_{PC-SERS})$ and the overall enhancement factor, using both effects together is $EF_{Tot}$=100$(I_{PC-SERS}t_0)/(I_0 t_{PC-SERS})$. For these experiments $t_0$=600 sec, $t_{Nano}$=50 sec, and $t_{PC-SERS}$=50 sec.

Figure 4A:
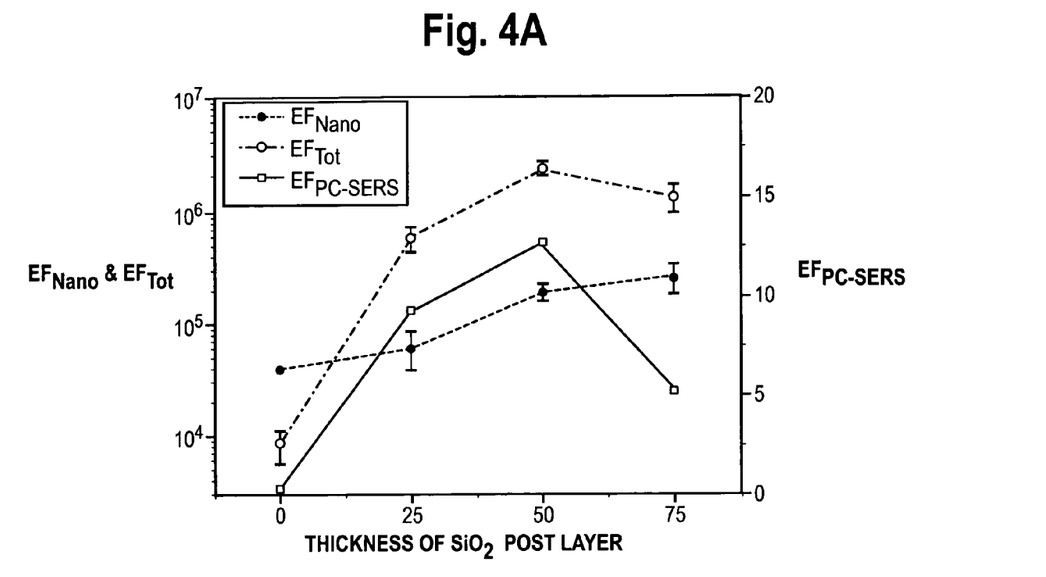
FIG. 4(a) is a graph showing the effects on SERS Enhancement Factor $(EF)_{Nano}$, $EF_{PC-SERS}$, and $EF_{Tot}$ for varying thickness of a $SiO_2$ post layer for a fixed Ag cap thickness of 40 nm.
Figure 4B:
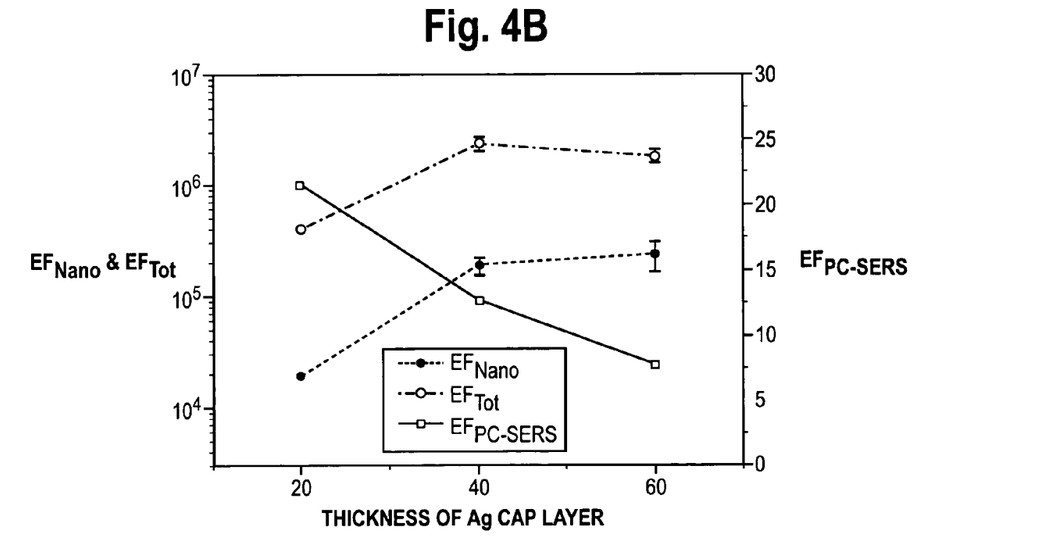
FIG. 4(b) is a graph showing the SERS Enhancement Factor (EF) for those varying thickness of Ag cap layer for a fixed $SiO_2$ post thickness of 50 nm.

FIG. 4(a) shows the effects of SiO$_2$ post thickness on $EF_{Nano}$, $EF_{PC-SERS}$, and $EF_{Tot}$ for a fixed Ag cap thickness of 40 nm, and variable SiO$_2$ post height. The $EF_{Nano}$ of GL-SERS substrates increased with increasing thickness of the SiO$_2$ post. However the maximum $EF_{PC-SERS}$ is obtained with a SiO$_2$ post height of 50 nm because the guided mode resonance of the PC degrades as the metal becomes too close to the PC surface. The $EF_{PC-SERS}$ for a 75 nm SiO$_2$ post is lower than that at 50 nm, because the intensity of resonant near-field of the PC decays exponentially with distance from the PC surface. FIG. 4(b) shows the effects of varying Ag cap thickness on $EF_{Nano}$, $EF_{PC-SERS}$, and $EF_{Tot}$ for a fixed SiO$_2$ post thickness of 50 nm. By increasing the thickness of Ag cap layer, the $EF_{Nano}$ on the GL-SERS substrate is increased. However, thicker Ag nanorods prevent light from reaching the PC surface, resulting in a reduced resonant EM near-field on the PC surface. Experimentally, we observe that $EF_{PC-SERS}$ decreased from 21.4× to 7.8× as Ag cap thickness increased from 20 to 60 nm.

In summary, this example embodiment demonstrates a PC-SERS substrate with SiO$_2$—Ag "Post-Cap" nanostructures and demonstrated the PC-SERS substrate can substantially enhance SERS sensitivity. Using the PC-SERS substrate having 50 nm SiO$_2$ posts and 40 nm Ag caps, a SERS EF of 2.34 10$^6$ was obtained. The SERS EF combines the effect of the SiO$_2$—Ag "Post-Cap" nanostructure with the resonant near-field of the PC, where the additional SERS EF attributable to the PC was as high as 21.4×. Since the intensity of resonant near-field of the PC is affected by the Q-factor (Q factor=30 to 10), and the Q-factor of the PC reported in this study is relatively low, the development of PC-SERS substrates with higher Q-factor for achieving greater enhancement will be pursued in the future.

As noted above, other embodiments of metallic nanostructures 24 of FIG. 1 can be applied to PC surfaces to enhance the SERS signals. For example, metallic films deposited over close-packed surface of nanospheres (also called "Ag Film Over Nanospheres" or AgFON) as disclosed in the work of Van Duyne), arrays of metallic nanotriangles, metallic nanorods, metallic nanohelices, arrays of metallic nanospheres, roughened metal surfaces, or other SERS-acvtive surface can be applied to a PCT to magnify or enhance the SERS signal.

I claim:

1. A method for performing surface enhanced Raman spectroscopy (SERS) with enhanced sensitivity, comprising the steps of:

providing an optical resonator device having a separate metal nanostructure formed on a surface of the optical resonator device, illuminating the optical resonator device with light to produce an enhanced resonant electric field in the optical resonator device; and coupling the enhanced electric field to the metal nanostructure, wherein the optical resonator comprises a photonic crystal, and wherein the metal nanostructure is selected from the group of nanostructures consisting of: a nanostructure formed on a dielectric support deposited on the photonic crystal; a metallic film deposited over close-packed surface of nanospheres; arrays of metallic nanotriangles; metallic nanorods; metallic nanohelices; arrays of metallic nanospheres; and roughened metal surfaces; and wherein the metal nanostructure comprises a nanostructure formed on a dielectic support deposited on the photonic crystal, and wherein the dielectric support comprises a post.

2. The method of claim 1, wherein the optical resonator device is incorporated into a liquid media handling device selected from the group of liquid media handling devices consisting of microscope slides, microfluidic channels, microtiter plates, flasks, product containers, Petri dishes, tubing and test tubes.

3. A method for performing surface enhanced Raman spectroscopy (SERS) with enhanced sensitivity, comprising the steps of:

providing an optical resonator device having a separate metal nanostructure formed on a surface of the optical resonator device, illuminating the optical resonator device with light to produce an enhanced resonant electric field in the optical resonator device; and coupling the enhanced electric field to the metal nanostructure;

wherein the optical resonator comprises a photonic crystal, and wherein the metal nanostructure is selected from the group of nanostructures consisting of: a nanostructure formed on a dielectric support deposited on the photonic crystal; a metallic film deposited over close-packed surface of nanospheres; arrays of metallic nanotriangles; metallic nanorods; metallic nanohelices; arrays of metallic nanospheres; and roughened metal surfaces; and wherein the metal nanostructure comprises a nanostructure formed on a dielectic support deposited on the photonic crystal, and wherein the dielectric support is formed from a dielectric material selected from the group of dielectric materials consisting of SiO2, silicon nitride, TiO2 and TaO.

4. The method of claim 3, wherein the optical resonator device is incorporated into a liquid media handling device selected from the group of liquid media handling devices consisting of microscope slides, microfluidic channels, microtiter plates, flasks, product containers, Petri dishes, tubing and test tubes.

5. A surface enhanced Raman spectroscopy sensor comprising:

an optical resonator having a separate metal nanostructure formed on a surface of the optical resonator, wherein an enhanced resonant electric field produced by the optical resonator in response to in-coupled incident radiation is coupled to the metal nanostructure, thereby increasing the sensitivity of the device to surface enhanced Raman spectroscopy signals for a molecule deposited on the said metal nanostructure;

wherein the optical resonator comprises a photonic crystal, and further comprising a dielectric support deposited on the surface of the photonic crystal and wherein the metal nanostructure is deposited on the dielectric support.

6. The sensor of claim 5, wherein the dielectric support comprises a post.

7. The sensor of claim 5, wherein the dielectric support is selected from the group of dielectric material consisting of SiO2, silicon nitride, TiO2 and TaO.

8. The sensor of claim 5, wherein the SERS sensor is incorporated into a liquid media handling device selected from the group of liquid media handling devices consisting of microscope slides, microfluidic channels, microtiter plates, flasks, product containers, Petri dishes, tubing and test tubes.

* * * * *